May 21, 1963 P. ECKE Plant Pat. 2,261
POINSETTIA PLANT
Filed Oct. 27, 1961
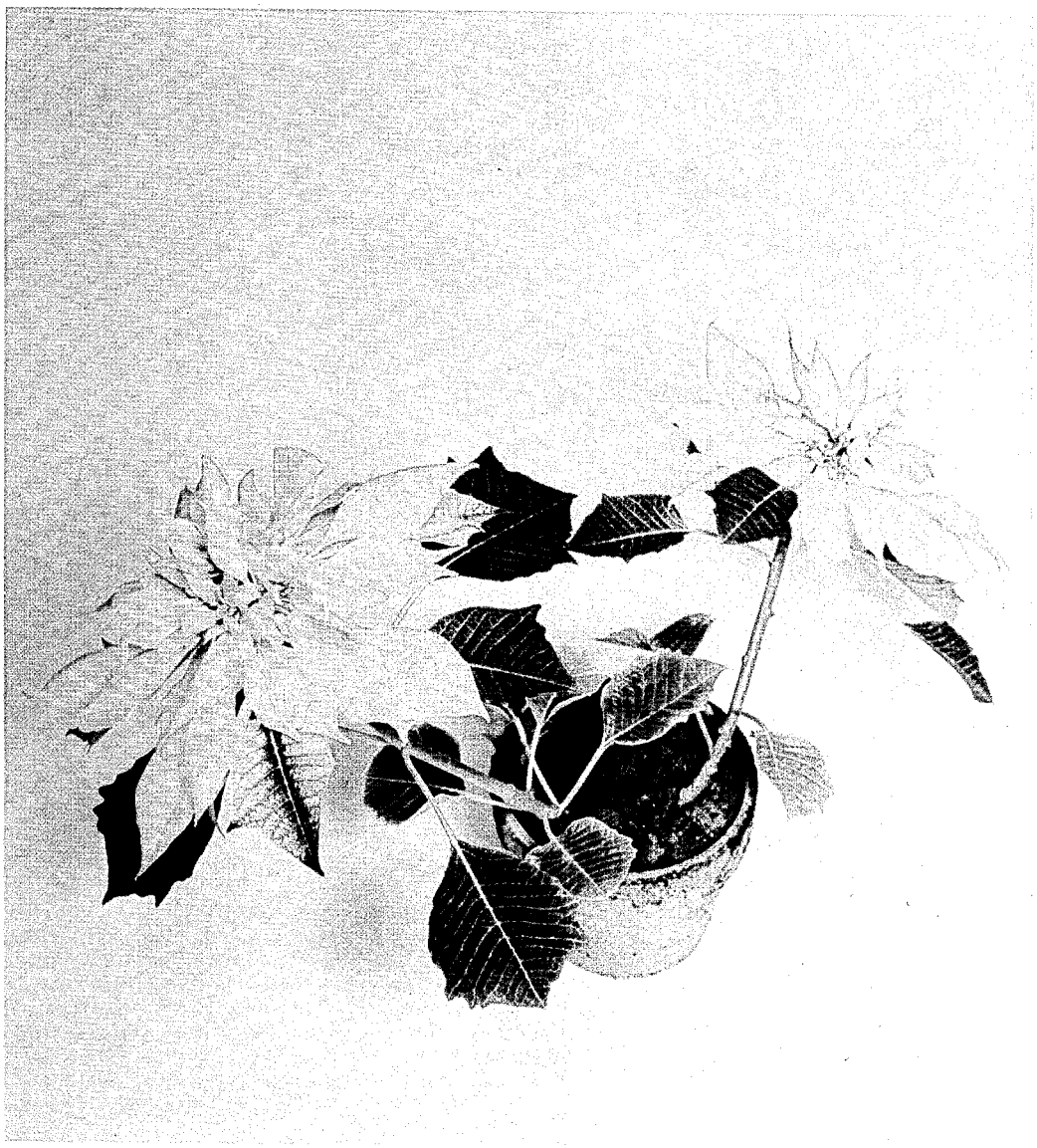
INVENTOR
Paul Ecke
by Wm. S. Graham
Attorney United States Patent Office Plant Pat. 2,261
Patented May 21, 1963

2,261
POINSETTIA PLANT

Paul Ecke, P.O. Box 488, Encinitas, Calif.

Filed Oct. 27, 1961, Ser. No. 148,300
1 Claim. (Cl. 47—60)

The subject of the present invention or discovery is a new and distinct variety of poinsettia plant (*Euphorbia pulcherrima*) originating as a cultivated sport. Broadly, this new variety of poinsettia plant is distinguishable from its parent plant, as well as from other known varieties, mainly by the pink, double rosette structure of bract formation and, to a lesser degree, by relatively thin, tough bracts, which facilitate shipping and minimize damage in such shipping and in handling.

The accompanying illustration, forming a part of this application, graphically shows this new variety in color at substantially full maturity or optimum, the illustration being a prespective view taken from an angle above the plant and, therefore, illustrating the double rosette formation of the bracts, as well as the foliage leaves, substantially as a full face view.

The colors referred to herein correspond approximately with those shown in "Dictionary of Color" by Maerz & Paul (first edition, 1930), and identified by the common color names and by the plate of said color standard, as recapitulated in tabular form herein.

The following description more fully sets forth the characteristics of this new variety.

*Parentage*

This new variety was originated, discovered and cultivated by me in a cultivated area of the glass house at my experimental and growing gardens at Encinitas, California, by means of cuttings. It originated as a cultivated sport of poinsettia plant of the variety commonly called the double "Henrietta Ecke," which is not patented, but has been known in the trade by that name for many years, and which has red bracts.

*Propagation*

This new variety of poinsettia plant has been repeatedly asexually reproduced and cultivated by me in my said glass house by cuttings, and successive reproductions thereof have remained true to type, and it has shown its herein described qualities and characteristics to be permanently fixed. In asexually reproducing this new variety, I found it satisfactory and efficient to cut pieces of stalk of softwood, substantially six inches in length, in or about the months of June, July and August, and to set one end of such cuttings in beds of sand in my glass house. After three or four weeks, the cuttings are well rooted and may be transferred to individual pots. My experience has been that the optimum temperature for growing under glass is on the order of 62 to 65 degrees F., night temperature, the daytime temperature being warmer, such as 70 to 75 degrees F., and subject to the varying conditions of light, heat, thickness of glass, cultivation, character of soil, fertilizer, and pruning or pinching.

*Habits of Growth*

This new variety of poinsettia plant develops its growth somewhat more rapidly than the normal average growth of poinsettia plants and will mature to optimum from about December 5th to December 20th and produces the optimum of its bract involucre at that same period of time. The bracts maintain their optimum for three to four weeks. This new variety is hardy and healthy in growth, and its rate of growth may be characterized as approximately average. This new variety seems to have an unusual resistance to disease and other detrimental factors and influences.

More particularly, this new variety is unusually resistant to a stem rot disease condition which is usually recognized as being caused by a root fungus designated rhizoctonia, and is also unusually resistant to a root rot condition caused by a fungus thielaviopsis, the detrimental factors of which are principally evidenced by leaf-drop of the foliage prior to complete maturity of the bract involucre and inflorescence. This resistance to disease and detrimental factors has been observed in this new variety when it has been grown side by side with other existing known varieties in the same field or in the same greenhouse condition, and the comparison of the new variety with known varieties has been observed over several years. These stated advantages of this new variety were established by observation of conditions present under usual and normal Southern California field culture conditions in which night-time temperatures in winter frequently go down into the lower forties (F.). In plants grown in the greenhouse the temperature is maintained substantially uniformly around sixty to sixty-five degrees (F.), and the same conditions would not be so readily observable as under field grown conditions and comparisons.

*Structure*

This new variety has a well-developed spread of root structure. The peduncle or main stalk is of a medium green color and of quite rugged strength, which makes this variety stand shipment better than average. The normal average height of the plant is between 3 and 4 feet. The internode space between foliage leaves is irregular, being generally spaced more closely together adjacent to the root than in the area more nearly to the bract involucre. At the top or axial end of the peduncle, a node is formed, from which grows a relatively small inflorescence and the characteristic bract involucre, the latter having a large number of small bracts closely clustered centrally about the inflorescence so that the inflorescence is substantially hidden at the center of the bract involucre, as will be further described.

*Bracts*

The principal novel characteristic of this new variety distinguishing it from known varieties is in the structural formation and the color of the bract involucre. In coloration, the bracts are of a pink-tinted rich rose pink color, which is closely similar to the color designated as Tyrian Rose at plate 24 and indicated 24/1 of the Horticultural Color Chart, issued by The British Color Council, and shown in Maerz and Paul "Dictionary of Color" standard at Plate 49, Letter L, number 1. At the center around the inflorescence, the bracts are closely centered, relatively short in length but of varying lengths and may be termed upstanding from the center of the involucre, being sufficiently numerous around the inflorescence so that the latter is substantially obscured from vision. Around these closely centered bracts and radiating from the center of the involucre, there are radical bracts which are much larger and longer and grow on substantially longer petioles. These radial bracts grow in a general plane forming a wreath or ring of radial bracts around the closely centered upstanding smaller bracts. In my prior plant patent, No. 1,207, dated July 28, 1953, for Poinsettia Plant, there are smaller bracts clustered at the center of the involucre and larger bracts radiating therefrom; but in that patent, the larger radiating bracts are much more numerous and relatively overlapping at adjacent edges, and droop over, whereby they tend to give the appearance of a rounded semi-sphere to the involucre as an entirety; whereas, in the present plant, the larger radiating bracts maintain a general plane, are relatively fewer in number, and each bract stands out separately with very little overlapping. The petioles of the bracts are substantially the same color as the blade portion of the bracts, and vary in length, but are predominantly relatively long. While the smaller bracts, clustered at the center of the involucre, are irregular in size and, to some extent, in shape, the larger radiating bracts are quite uniform in size and in shape, which is generally prolately ovate-cuminate.

The bracts are relatively thin, and are tough in texture, aiding greatly in elimination of bruising in shipment.

*Foliage*

The foliage leaves are arranged around the peduncle, the nodes thereof being quite closely spaced adjacent to the base, and being of greater and more uniform spacing between the base portion and the upper end of the peduncle, and the petioles radiate in stepped, staggered order from the peduncles. As in many varieties of poinsettia plants, the foliage leaves are not entirely uniform in shape, but are generally oblate-ovate at the pedicel-end, and have a plurality of oak-leaf points at the outer end. The petioles of the foliage leaves are rather long, and the venation is of herring-bone type. The color of the foliage leaves may be broadly described as medium gray green. Occasionally, but not sufficiently uniformly to be defined as a fixed characteristic of this new variety, one or two of the foliage leaves next adjacent the bracts will be splashed with color simulating the color of the bracts, as illustrated in respect of one of the two bract involucres shown herein but not shown in respect of the other illustracted bract involucre. This is not an uncommon phenomenon in known varieties of poinsettia plants.

*Inflorescence*

The inflorescence grows upon the axial free terminal end of the peduncle and centrally of the bract involucre. It is, to a large extent, substantially hidden from vision by the closely centered bracts, and the details are thereby largely obscured. The flower cyathium grows on short sub-acaulescent stems. As in a large number of varieties of poinsettia plants, the cyathium is of pale green color, small and not prominent, and the flower growing therefrom is orange yellow in color with a touch of crimson red center.

*Variations*

Different plants of this variety have an unusual similarity of adherence to characteristics and type herein described. However, there may be some variation in the characteristics of minor details, in comparison of plants growing in various localities, in different soils, and in different times of the year, varying temperatures, varying types of glass house, or out of doors.

*Color Tabulation*

The color designations according to the color plates of said "Dictionary of Color" are recapitulated in tabular form as follows:

| Part of plant | Non-technical designation of color | Dictionary of color | | |
|---|---|---|---|---|
| | | Plate | Letter | Number |
| Peduncle | Medium green | 18 | L | 8 |
| Bracts | Rose pink | 49 | L | 1 |
| Petioles of bracts | do | 49 | L | 1 |
| Foliage leaves | Medium gray green | 23 | J | 9 |
| INFLORESCENCE | | | | |
| (a) Cyathium | Pale green | 17 | I | 7 |
| (b) Flower | Orange yellow | 10 | L | 5 |
| (c) Center portion | Crimson red | 41 | L | 1 |

Having thus described the new variety of poinsettia plant of my invention, I claim:

A new and distinct variety of poinsettia plant, substantially as illustrated and described, characterized by bracts of a bright and vivid rose pink color, and by a bract involucre having a first group of bracts comprising relatively large prolately ovate-cuminate bracts, the predominating portion of which radiate on relatively long petioles from the center of the involucre as a wreath in generally planar form and providing in the involucre a relatively open center of said large bracts, and further characterized by a second group of similarly colored bracts which are relatively smaller in size and irregular in shape, which grow upstandingly and clustered at the center of the involucre, substantially filling the open center of the first groups of bracts and substantially obscuring the inflorescence from vision, the bracts being relatively thin and tough and thereby resistant to damage and bruising in shipment.

No references cited.